US006574502B2

(12) United States Patent
Hayashi

(10) Patent No.: US 6,574,502 B2
(45) Date of Patent: Jun. 3, 2003

(54) APPARATUS FOR DISPLAYING FLUORESCENCE IMAGES

(75) Inventor: Katsumi Hayashi, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 80 days.

(21) Appl. No.: 09/728,060

(22) Filed: Dec. 4, 2000

(65) Prior Publication Data

US 2001/0007920 A1 Jul. 12, 2001

(30) Foreign Application Priority Data

Dec. 2, 1999 (JP) .......................................... 11-342932

(51) Int. Cl.[7] .............................................. A61B 6/00
(52) U.S. Cl. ..................................................... 600/476
(58) Field of Search ................................. 600/160, 476, 600/477; 250/338.1, 339.01, 339.02, 339.06, 370.08, 370.09

(56) References Cited

U.S. PATENT DOCUMENTS

| 5,647,368 A | 7/1997 | Zeng et al. .................. 128/665 |
| 5,833,617 A | * 11/1998 | Hayashi ................... 250/461.1 |
| 6,371,908 B1 | * 4/2002 | Furusawa et al. ........... 600/160 |
| 6,422,994 B1 | * 7/2002 | Kaneko et al. ............. 600/160 |

FOREIGN PATENT DOCUMENTS

JP 9-327433 12/1997 ............ A61B/1/00

* cited by examiner

*Primary Examiner*—Sang Paik
(74) *Attorney, Agent, or Firm*—Sughrue Mion, PLLC

(57) ABSTRACT

Excitation light is irradiated to a region of interest in a living body, the excitation light causing the region of interest to produce intrinsic fluorescence. An image displaying system acquires image information in accordance with the intrinsic fluorescence and displays the acquired image information. The image displaying system comprises a light intensity detecting device for an entire measurement wavelength region of the intrinsic fluorescence, a light intensity detecting device for a partial measurement wavelength region of the intrinsic fluorescence, and a display device. The display device displays a display color in accordance with a ratio between the light intensity, which has been detected by the light intensity detecting device for the entire measurement wavelength region, and the light intensity, which has been detected by the light intensity detecting device for the partial measurement wavelength region. The display color is displayed by the utilization of an additive color mixture process.

5 Claims, 7 Drawing Sheets

APPARATUS FOR DISPLAYING FLUORESCENCE IMAGES

BACKGROUND OF THE INVENTION

1. Field of the Invention

This invention relates to an apparatus for displaying a fluorescence image, wherein a fluorescence image in accordance with characteristics of fluorescence, which is produced from a measuring site in a living body when the measuring site is exposed to excitation light, is displayed.

2. Description of the Related Art

There have heretofore been proposed apparatuses for displaying a fluorescence image by utilizing characteristics such that, in cases where excitation light having wavelengths falling within an excitation wavelength range for an intrinsic dye in a living body is irradiated to the living body, an intensity of fluorescence produced by the intrinsic dye in the living body varies for normal tissues and diseased tissues. With the proposed apparatuses for displaying a fluorescence image, excitation light having predetermined wavelengths is irradiated to a region of interest in a living body, the fluorescence produced by an intrinsic dye in the living body is detected, and the location and the infiltration range of diseased tissues are displayed as an image.

FIG. 10 shows typical fluorescence spectra of the fluorescence produced from normal tissues and the fluorescence produced from diseased tissues, which fluorescence spectra have been measured by the inventors. It is assumed that the thus produced fluorescence results from superposition of the fluorescence produced by various kinds of intrinsic dyes in the living body, such as FAD, collagen, fibronectin, and porphyrin. Ordinarily, when excitation light is irradiated to a region of interest in a living body, the fluorescence having a high intensity is produced by normal tissues, and the fluorescence having a low intensity is produced by diseased tissues. Therefore, in cases where information in accordance with the fluorescence intensity is displayed, a person who sees the displayed information is capable of recognizing the state of the diseased tissues. In many cases, the apparatuses for displaying a fluorescence image take on the form built in endoscopes, which are inserted into the body cavities, colposcopes, operating microscopes, or the like.

However, the aforesaid apparatuses for displaying a fluorescence image have the problems described below. Specifically, in cases where a region in a living body has protrusions and recesses, the distance between an excitation light irradiating system and the measuring site in the living body is not uniform. Therefore, it often occurs that the irradiance of the excitation light at the living body portion, which is exposed to the excitation light, is not uniform. The intensity of fluorescence is approximately in proportion to the irradiance of the excitation light, and the irradiance of the excitation light at the portion, which is exposed to the excitation light, is in inverse proportion to the square of the distance between the excitation light irradiating system and the portion, which is exposed to the excitation light. Accordingly, the problems occur in that diseased tissues, which are located close to the light source, produce the fluorescence having a higher intensity than the intensity of the fluorescence produced by normal tissues, which are located remote from the light source. The problems also occur in that the intensity of the fluorescence from normal tissues, which are located at a position inclined with respect to the excitation light, becomes low.

In order for the adverse effects of differences in measuring conditions, such as a measuring distance and a measuring angle, to be eliminated, there has been proposed an apparatus for displaying a fluorescence image by utilizing the characteristics such that a pattern of a fluorescence spectrum varies for the fluorescence produced from the normal tissues and the fluorescence produced from the diseased tissues. With the proposed apparatus for displaying a fluorescence image, as illustrated in FIG. 11, a quotient of division R/G is calculated from light intensity R of a red wavelength region and light intensity G of a green wavelength region. Also, information in accordance with the results of the division R/G is displayed on a monitor. In this manner, the location and the infiltration range of the diseased tissues are displayed as an image.

With the proposed apparatus for displaying a fluorescence image, the term of the fluorescence intensity depending upon the distance between the excitation light source and the region of interest in the living body and the distance between the region of interest in the living body and the fluorescence receiving means is canceled by the division R/G. Therefore, the term of the fluorescence intensity depending upon the distance between the excitation light source and the region of interest in the living body and the distance between the region of interest in the living body and the fluorescence receiving means can be ignored. However, the light intensity of the intrinsic fluorescence components of the green region in the intrinsic fluorescence produced from the diseased tissues is low. As a result, it often occurs that division by a value of zero occurs, and the operation becomes unstable.

An apparatus for displaying a fluorescence image as illustrated in FIG. 12 has been proposed in, for example, Japanese Unexamined Patent Publication No. 9(1997)-327433. With the proposed apparatus for displaying a fluorescence image, excitation light L9 is produced by an excitation light source 401 and is irradiated to a measuring site 60. Fluorescence L10, which is produced from the measuring site 60 when the measuring site 60 is exposed to the excitation light L9, is acquired via an endoscope 402. Fluorescence components of a red wavelength region and fluorescence components of a green wavelength region are selected from the fluorescence L10 by use of mirrors 403, 404 and filters 405, 406. The fluorescence components of the red wavelength region and the fluorescence components of the green wavelength region are detected respectively by high-sensitivity charge coupled device (CCD) image sensors 407 and 408. An image signal representing the fluorescence components of the red wavelength region, which image signal has been obtained from the CCD image sensor 408, is fed into an R signal input terminal of a color monitor 409. Also, an image signal representing the fluorescence components of the green wavelength region, which image signal has been obtained from the CCD image sensor 407, is fed into a G signal input terminal and a B signal input terminal of the color monitor 409. In this manner, relative intensities of the image signal representing the fluorescence components of the red wavelength region and the image signal representing the fluorescence components of the green wavelength region are displayed as a change in color on the color monitor 409.

With the apparatus for displaying a fluorescence image proposed in Japanese Unexamined Patent Publication No. 9(1997)-327433, there is no risk that division by a value of zero will occur. Also, the display color on the monitor changes in accordance with a ratio between the light intensity of the red wavelength region and the light intensity of the green wavelength region. Therefore, the person who sees the image displayed on the monitor is capable of recognizing the state of the diseased tissues in accordance with the display color.

However, the fluorescence, which is produced from the living body tissues when the living body tissues are exposed to the excitation light, is weak. With the apparatus for displaying a fluorescence image proposed in Japanese Unexamined Patent Publication No. 9(1997)-327433, only the light intensity of the red wavelength region and the light intensity of the green wavelength region are detected from the weak fluorescence, and a fluorescence image is formed. Therefore, the apparatus for displaying a fluorescence image proposed in Japanese Unexamined Patent Publication No. 9(1997)-327433 has the problems in that the efficiency, with which the fluorescence is utilized, cannot be kept high, adverse effects of photon noise, and the like, are apt to occur during photoelectric conversion for the detection of the light intensities, and a signal-to-noise ratio of the fluorescence image cannot be kept high.

SUMMARY OF THE INVENTION

The primary object of the present invention is to provide an apparatus for displaying a fluorescence image, wherein image information in accordance with fluorescence, which is produced from living body tissues when the living body tissues are exposed to excitation light, is acquired and displayed, such that an efficiency, with which the fluorescence is utilized, is enhanced, and a signal-to-noise ratio of a displayed fluorescence image is kept high.

Another object of the present invention is to provide an apparatus for displaying a fluorescence image, wherein a fluorescence image is displayed such that recognition as to whether fluorescence, which has been produced from a measuring site, is the fluorescence produced from normal tissues or the fluorescence produced from diseased tissues is capable of being made with a high reliability.

The present invention provides a first apparatus for displaying a fluorescence image, comprising:
  i) excitation light irradiating means for irradiating excitation light to a region of interest in a living body, the excitation light causing the region of interest to produce intrinsic fluorescence, and
  ii) image displaying means for acquiring image information in accordance with the intrinsic fluorescence, which is produced from the region of interest when the region of interest is exposed to the excitation light, and displaying the acquired image information,
  wherein the image displaying means comprises:
    a) light intensity detecting means for an entire measurement wavelength region, which light intensity detecting means detects a light intensity of intrinsic fluorescence components of the intrinsic fluorescence, which intrinsic fluorescence components have wavelengths falling within the entire measurement wavelength region,
    b) light intensity detecting means for a partial measurement wavelength region, which light intensity detecting means detects a light intensity of intrinsic fluorescence components of the intrinsic fluorescence, which intrinsic fluorescence components have wavelengths falling within either one of a comparatively short wavelength region and a comparatively long wavelength region, and
    c) display means for displaying a display color in accordance with a ratio between the light intensity, which has been detected by the light intensity detecting means for the entire measurement wavelength region, and the light intensity, which has been detected by the light intensity detecting means for the partial measurement wavelength region, the display color being displayed by the utilization of an additive color mixture process.

In the first apparatus for displaying a fluorescence image in accordance with the present invention, the light intensity detecting means for the entire measurement wavelength region should preferably detect a light intensity of intrinsic fluorescence components of the intrinsic fluorescence, which intrinsic fluorescence components have wavelengths falling within an entire visible wavelength region excluding the vicinity of the wavelength region of the excitation light.

The present invention also provides a second apparatus for displaying a fluorescence image, comprising:
  i) excitation light irradiating means for irradiating excitation light to a region of interest in a living body, the excitation light causing the region of interest to produce intrinsic fluorescence, and
  ii) image displaying means for acquiring image information in accordance with the intrinsic fluorescence, which is produced from the region of interest when the region of interest is exposed to the excitation light, and displaying the acquired image information,
  wherein the image displaying means comprises:
    a) light intensity detecting means for a red region, which light intensity detecting means detects a light intensity of intrinsic fluorescence components of the intrinsic fluorescence, which intrinsic fluorescence components have wavelengths falling within the red wavelength region,
    b) light intensity detecting means for a green region, which light intensity detecting means detects a light intensity of intrinsic fluorescence components of the intrinsic fluorescence, which intrinsic fluorescence components have wavelengths falling within the green wavelength region,
    c) light intensity detecting means for a blue region, which light intensity detecting means detects a light intensity of intrinsic fluorescence components of the intrinsic fluorescence, which intrinsic fluorescence components have wavelengths falling within the blue wavelength region, and
    d) display means for displaying a display color in accordance with a ratio among the light intensity, which has been detected by the light intensity detecting means for the red region, the light intensity, which has been detected by the light intensity detecting means for the green region, and the light intensity, which has been detected by the light intensity detecting means for the blue region, the display color being displayed by the utilization of an additive color mixture process.

In the second apparatus for displaying a fluorescence image in accordance with the present invention, a sum of the light intensity, which has been detected by the light intensity detecting means for the red region, the light intensity, which has been detected by the light intensity detecting means for the green region, and the light intensity, which has been detected by the light intensity detecting means for the blue region, should preferably be the light intensity of intrinsic fluorescence components of the intrinsic fluorescence, which intrinsic fluorescence components have wavelengths falling within an entire fluorescence wavelength region excluding the wavelength region of the excitation light.

The first and second apparatuses for displaying a fluorescence image in accordance with the present invention should preferably be modified such that the display means is provided with a matrix operation circuit for transforming each of the light intensities into color signals and is constituted such that a color corresponding to each of the light intensities is capable of being selected arbitrarily by appropriately setting coefficients of an operation formula in the matrix operation circuit.

The detection of the light intensity of the intrinsic fluorescence components of the intrinsic fluorescence, which intrinsic fluorescence components have wavelengths falling within each wavelength region, by each of the light intensity detecting means may be performed with one of various techniques. For example, the intrinsic fluorescence having been produced from the measuring site may be separated by optical filters, or the like, into groups of the intrinsic fluorescence components having wavelengths falling within desired wavelength regions, which are to be employed ultimately, and the light intensities of the thus separated groups of the intrinsic fluorescence components may be detected respectively. Alternatively, the light intensity of intrinsic fluorescence components having wavelengths falling within a predetermined wavelength region, which is different in part from the desired wavelength region to be employed ultimately, may be detected, and the light intensity of the intrinsic fluorescence components having wavelengths falling within the desired wavelength region to be employed ultimately may be calculated from the detected light intensity with operation processing, such as adding and subtracting operations.

With the first apparatus for displaying a fluorescence image in accordance with the present invention, the light intensity of the intrinsic fluorescence components, which have wavelengths falling within the entire measurement wavelength region, and the light intensity of the intrinsic fluorescence components, which have wavelengths falling within either one of the comparatively short wavelength region and the comparatively long wavelength region, are detected. Also, the display color in accordance with the ratio between the two light intensities is displayed by the utilization of the additive color mixture process. In this manner, the light intensity of the intrinsic fluorescence components of the intrinsic fluorescence having been produced from the measuring site, which intrinsic fluorescence components have wavelengths falling within the entire measurement wavelength region, is capable of being utilized. Therefore, the efficiency, with which the intrinsic fluorescence is utilized, is capable of being enhanced, and the signal-to-noise ratio of the displayed fluorescence image is capable of being kept high.

Also, with the first apparatus for displaying a fluorescence image in accordance with the present invention, wherein the entire measurement wavelength region is the entire visible wavelength region excluding the vicinity of the wavelength region of the excitation light, the detection of the light intensity is not obstructed by the excitation light, and the intrinsic fluorescence having been produced from the measuring site is capable of being utilized efficiently.

With the second apparatus for displaying a fluorescence image in accordance with the present invention, the display color in accordance with the ratio among the light intensity of the intrinsic fluorescence components of the intrinsic fluorescence having been produced from the measuring site in the living body exposed to the excitation light, which intrinsic fluorescence components have wavelengths falling within the red wavelength region, the light intensity of the intrinsic fluorescence components, which have wavelengths falling within the green wavelength region, and the light intensity of the intrinsic fluorescence components, which have wavelengths falling within the blue wavelength region, is displayed by the utilization of the additive color mixture process. Therefore, the efficiency, with which the intrinsic fluorescence having been produced from the measuring site is utilized, is capable of being enhanced. Accordingly, the signal-to-noise ratio of the displayed fluorescence image is capable of being kept high. Also, a fine difference in light intensity between wavelength regions of the intrinsic fluorescence having been produced from the measuring site is capable of being displayed as a difference in tint.

Further, imaging means for detecting the fluorescence image is capable of being utilized also as the imaging means for an ordinary image. Therefore, the production cost of the apparatus for displaying a fluorescence image is capable of being kept low.

With the second apparatus for displaying a fluorescence image in accordance with the present invention, the sum of the light intensity of the intrinsic fluorescence components, which have wavelengths falling within the red wavelength region, the light intensity of the intrinsic fluorescence components, which have wavelengths falling within the green wavelength region, and the light intensity of the intrinsic fluorescence components, which have wavelengths falling within the blue wavelength region, may be the light intensity of the intrinsic fluorescence components, which have wavelengths falling within the entire fluorescence wavelength region excluding the wavelength region of the excitation light. In such cases, the detection of the light intensity is not obstructed by the excitation light, and the intrinsic fluorescence having been produced from the measuring site is capable of being utilized efficiently.

With the first and second apparatuses for displaying a fluorescence image in accordance with the present invention, the display means may be provided with the matrix operation circuit for transforming each of the light intensities into color signals and may be constituted such that a tint corresponding to each of the light intensities is capable of being selected arbitrarily by appropriately setting the coefficients of the operation formula in the matrix operation circuit. In such cases, the display color is capable of being adjusted so as to match with the sensitivity of the human eyes. Therefore, the person who sees the displayed fluorescence image is capable of recognizing with an enhanced reliability as to whether the fluorescence, which has been produced from the measuring site, is the fluorescence produced from the normal tissues or the fluorescence produced from the diseased tissues.

DESCRIPTION OF THE PREFERRED EMBODIMENTS

The present invention will hereinbelow be described in further detail with reference to the accompanying drawings.

Figure 1:
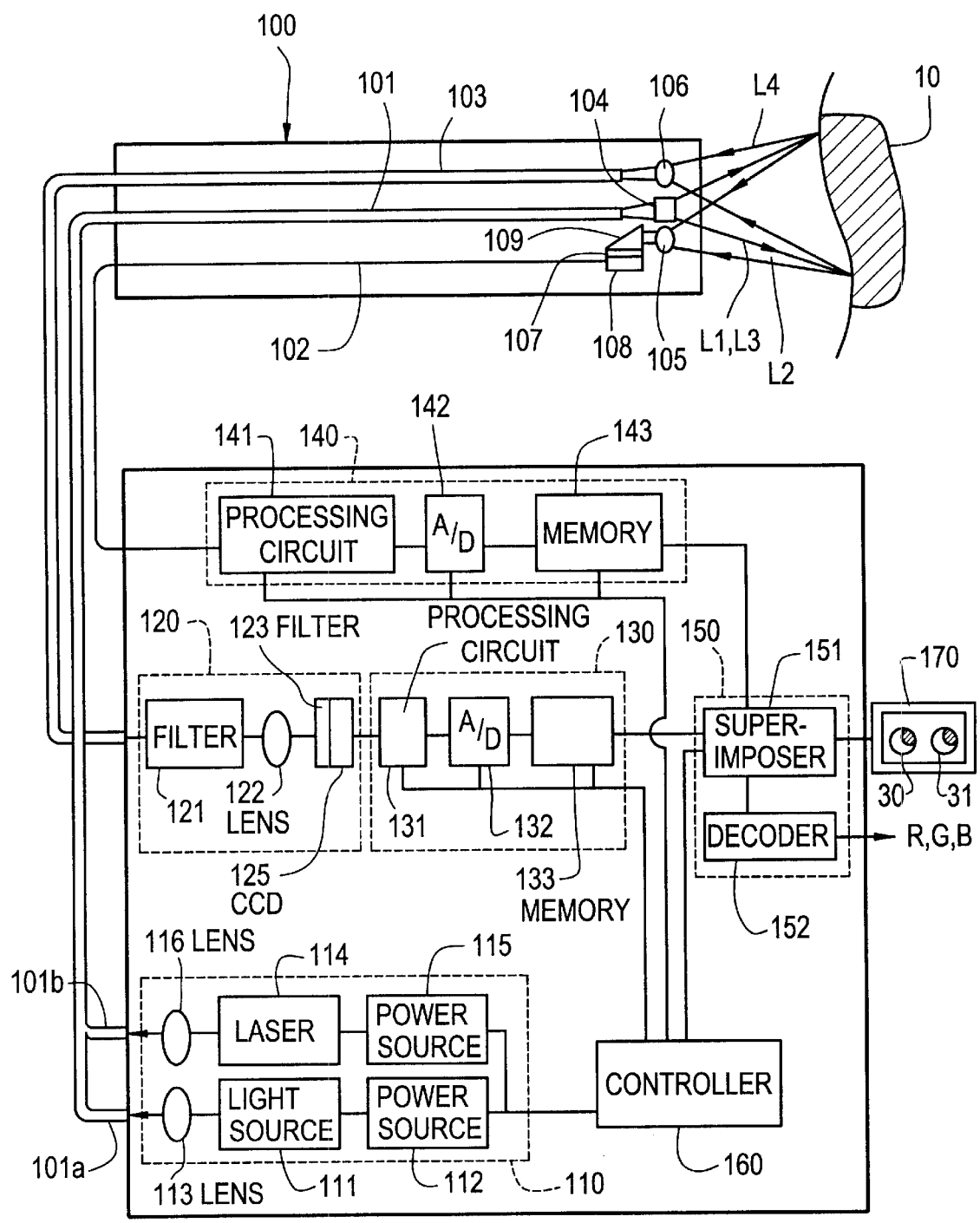
FIG. 1 is a schematic view showing an endoscope system, in which a first embodiment of the apparatus for displaying a fluorescence image in accordance with the present invention is employed.

Firstly, an endoscope system, in which a first embodiment of the apparatus for displaying a fluorescence image in accordance with the present invention is employed, will be described hereinbelow with reference to FIG. 1 to FIG. 6. FIG. 1 is a schematic view showing the endoscope system, in which the first embodiment of the apparatus for displaying a fluorescence image in accordance with the present invention is employed. In the endoscope system, in which the first embodiment of the apparatus for displaying a fluorescence image in accordance with the present invention is employed, excitation light is irradiated to a measuring site in a living body, the excitation light causing the measuring site to produce fluorescence. The fluorescence produced from the measuring site is two-dimensionally detected with an image fiber and received by a high-sensitivity image sensor. Also, light intensity of fluorescence components of the fluorescence, which fluorescence components have wavelengths falling within a wavelength region of 430 nm to 530 nm, and light intensity of fluorescence components of the fluorescence, which fluorescence components have wavelengths falling within an entire measurement wavelength region, are detected. Further, a display color in accordance with the ratio between the two detected light intensities is displayed on a monitor by the utilization of the additive color mixture process.

The endoscope system, in which the first embodiment of the apparatus for displaying fluorescence information in accordance with the present invention is employed, comprises an endoscope 100 to be inserted into a region of a patient, which region is considered as being a diseased part, and an illuminating unit 110 provided with light sources for producing white light, which is used when an ordinary image is to be displayed, and the excitation light, which is used when fluorescence information is to be displayed. The endoscope system also comprises a fluorescence imaging unit 120 for receiving the fluorescence, which is produced from the measuring site in the living body when the measuring site is exposed to the excitation light, and detecting the image of the fluorescence. The endoscope system further comprises a fluorescence image processing unit 130 for performing image processing for displaying the fluorescence image, which has been detected by the fluorescence imaging unit 120, as a fluorescence image in a display color in accordance with the ratio between light intensities of fluorescence components of the fluorescence, which fluorescence components have wavelengths falling within predetermined wavelength regions. The endoscope system still further comprises an ordinary image processing unit 140 for performing image processing for displaying an ordinary image as a color image. The endoscope system also comprises a display image processing unit 150 for superimposing the ordinary image and the fluorescence image one upon the other. The endoscope system further comprises a controller 160, which is connected to the respective units and controls operation timings. The endoscope system still further comprises a monitor 170 for displaying the display images, which have been obtained from the processing performed by the display image processing unit 150.

A light guide 101, a CCD cable 102, and an image fiber 103 extend in the endoscope 100 up to a leading end of the endoscope 100. An illuminating lens 140 is located at a leading end of the light guide 101, i.e. at the leading end of the endoscope 100. An objective lens 105 is located at a leading end of the CCD cable 102, i.e. at the leading end of the endoscope 100. The image fiber 103 is constituted of quartz glass fibers, and a converging lens 106 is located at a leading end of the image fiber 103. A CCD image sensor 108 is connected to the leading end of the CCD cable 102. A mosaic filter 107, which comprises three primary color optical filters arrayed in a mosaic form, is combined with the CCD image sensor 108. Also, a prism 109 is mounted on the CCD image sensor 108.

Figure 2:
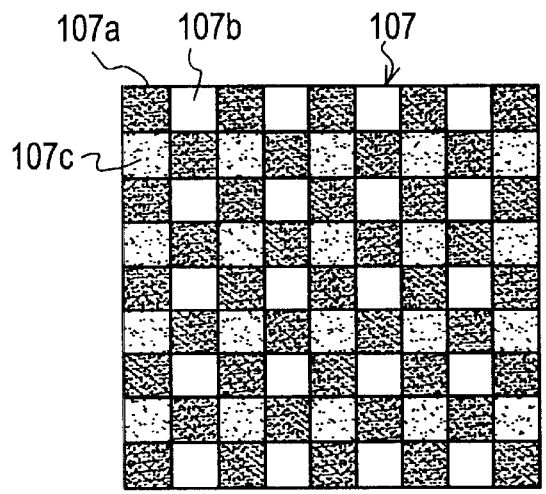
FIG. 2 is a schematic view showing a mosaic filter for an ordinary image employed in the endoscope system, in which the first embodiment of the apparatus for displaying a fluorescence image in accordance with the present invention is employed.

As illustrated in FIG. 2, the mosaic filter 107 comprises optical filters 107a, 107a, . . . , optical filters 107b, 107b, . . . , and optical filters 107c, 107c, . . . , which are arrayed alternately. The optical filters 107a, 107a, . . . are band pass filters for transmitting only light having wavelengths falling within the range of 400 nm to 500 nm. The optical filters 107b, 107b, . . . are band pass filters for transmitting only light having wavelengths falling within the range of 500 nm to 600 nm. The optical filters 107c,, 107c,, . . . are band pass filters for transmitting only light having wavelengths falling within the range of 600 nm to 700 nm.

The light guide 101 comprises a white light guide 101a, which is constituted of a compound glass fiber, and an excitation light guide 101b, which is constituted of a quartz glass fiber. The white light guide 101a and the excitation light guide 101b are bundled together in a cable-like form to constitute the light guide 101. The white light guide 101a and the excitation light guide 101b are connected to the illuminating unit 110. A tail end of the CCD cable 102 is connected to the ordinary image processing unit 140. A tail end of the image fiber 103 is connected to the fluorescence imaging unit 120.

The illuminating unit 110 comprises a white light source 111 for producing white light L1, which is used when an ordinary image is to be displayed, and an electric power source 112, which is electrically connected to the white light source 111. The illuminating unit 110 also comprises a GaN type of semiconductor laser 114 for producing excitation light L3, which is used when a fluorescence image is to be displayed, and an electric power source 115, which is electrically connected to the GaN type of semiconductor laser 114.

The fluorescence imaging unit 120 comprises an excitation light cut-off filter 121 for filtering out light, which has wavelengths falling within a wavelength region of at most 430 nm in the vicinity of the wavelength of the excitation light L3, from fluorescence L4 having passed through the image fiber 103. The fluorescence imaging unit 120 also comprises a CCD image sensor 125, which is constituted of a cooled, back exposure type of CCD image sensor. The CCD image sensor 125 is combined with a mosaic filter 123, which comprises two kinds of optical filters combined with each other in a mosaic-like form.

Figure 3:
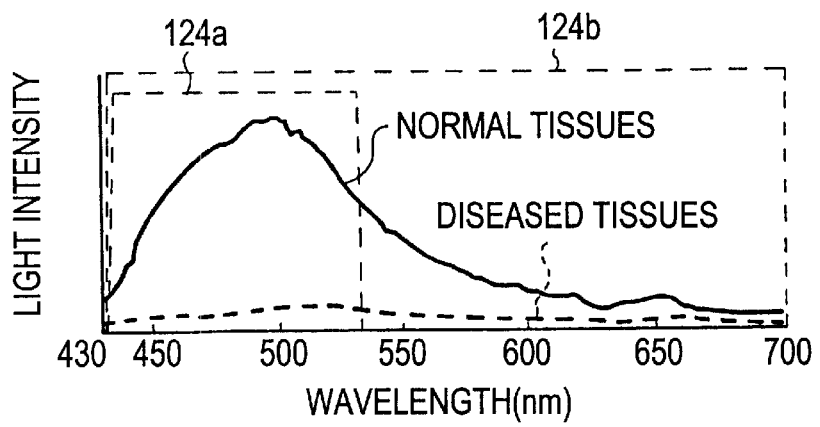
FIG. 3 is a graph showing transmission wavelength regions of optical filters constituting a mosaic filter for a fluorescence image employed in the endoscope system, in which the first embodiment of the apparatus for displaying a fluorescence image in accordance with the present invention is employed.
Figure 4:
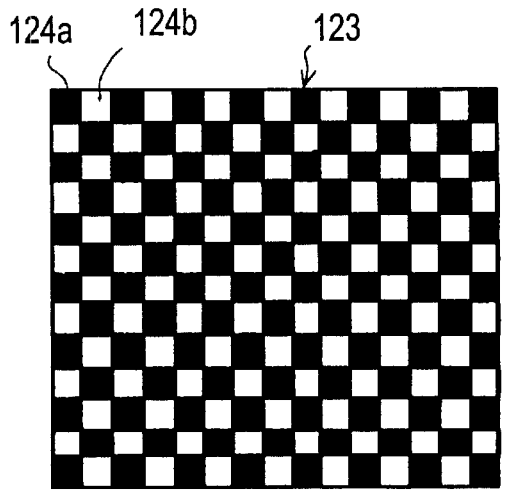
FIG. 4 is a schematic view showing the mosaic filter for a fluorescence image employed in the endoscope system, in which the first embodiment of the apparatus for displaying a fluorescence image in accordance with the present invention is employed.

As illustrated in FIG. 4, the mosaic filter 123 is constituted of optical filters 124a, 124a, . . . and blank areas 124b, 124b, . . . The optical filters 124a, 124a, . . . are band-pass filters, which transmit only light having wavelengths falling within a wavelength region of 430 nm to 530 nm. The blank areas 124b, 124b, . . . transmit light having wavelengths falling within the entire measurement wavelength region. The transmission wavelength regions of the optical filters 124a, 124a, . . . and the blank areas 124b, 124b, are illustrated in FIG. 3.

The fluorescence image processing unit 130 comprises a signal processing circuit 131 for forming pseudo color image signals from image signal values, which have been obtained from the CCD image sensor 125. The fluorescence image processing unit 130 also comprises an analog-to-digital converting circuit 132 for digitizing the pseudo color image signals, which have been obtained from the signal processing circuit 131. The fluorescence image processing unit 130 further comprises a fluorescence image memory 133 for storing the digital pseudo color image signals, which have been obtained from the analog-to-digital converting circuit 132.

The ordinary image processing unit 140 comprises a signal processing circuit 141 for forming color image signals from image signal values, which have been obtained from the CCD image sensor 108. The ordinary image processing unit 140 also comprises an analog-to-digital converting circuit 142 for digitizing the color image signals, which have been obtained from the signal processing circuit 141. The ordinary image processing unit 140 further comprises an ordinary image memory 143 for storing the digital color image signals, which have been obtained from the analog-to-digital converting circuit 142.

The display image processing unit 150 comprises a superimposer 151 for superimposing the pseudo color image signals, which have been received from the fluorescence image memory 133, and the color image signals, which have been received from the ordinary image memory 143, one upon the other. The display image processing unit 150 also comprises an RGB decoder 152 for transforming the superimposed image signals into R, G, and B display signals.

How the endoscope system, in which the first embodiment of the apparatus for displaying a fluorescence image in accordance with the present invention is employed, operates will be described hereinbelow. Firstly, how the endoscope system operates when an ordinary image is to be displayed will be described hereinbelow.

When an ordinary image is to be displayed, the electric power source 112 for the white light source 111 is driven in accordance with a control signal fed from the controller 160, and the white light L1 is produced by the white light source 111. The white light L1 passes through a lens 113 and impinges upon the white light guide 101a. The white light L1 is guided through the white light guide 101a to the leading end of the endoscope 100, passes through the illuminating lens 104, and is irradiated to a measuring site 10. The white light L1 is reflected as reflected light L2 from the measuring site 10. The reflected light L2 is converged by the objective lens 105 and reflected by the prism 109. The reflected light L2 then passes through the mosaic filter 107, and an image of the reflected light L2 is formed on the CCD image sensor 108.

In the signal processing circuit 141, the color image signals are formed in the manner described below from the image signal values, which have been obtained from the CCD image sensor 108. Specifically, matrix operations according to an NTSC method are performed by utilizing light intensity B1 of light components, which have wavelengths falling within the blue wavelength region and have passed through the optical filters 107a, 107a, . . . , light intensity G1 of light components, which have wavelengths falling within the green wavelength region and have passed through the optical filters 107b, 107b, . . . , and light intensity R1 of light components, which have wavelengths falling within the red wavelength region and have passed through the optical filters 107c, 107c, . . . , and by utilizing the image signal values corresponding to pixels adjacent to each pixel. The matrix operations according to the NTSC method are performed with Formula (1) shown below to calculate a luminance signal Y1 and color difference signals R1−Y1 and B1−Y1, which act as the color image signals.

$$\begin{bmatrix} Y1 \\ R1 - Y1 \\ B1 - Y1 \end{bmatrix} = \begin{bmatrix} 0.3 & 0.59 & 0.11 \\ 0.7 & -0.59 & -0.11 \\ -0.3 & -0.59 & 0.89 \end{bmatrix} \begin{bmatrix} R1 \\ G1 \\ B1 \end{bmatrix} \quad (1)$$

Specifically, calculations are made with the formulas shown below.

Y1=0.30R1+0.59G1+0.11B1

R1−Y1=0.70R1−0.59G1−0.11B1

B1−Y1=−0.30R1−0.59G1+0.89B1

The luminance signal Y1 is determined so as to match with the sensitivity of the human eyes with respect to color.

In the NTSC method, actually, the color difference signals are transformed into chromaticity signals I and Q with linear transform so as to correspond to the visual resolution of the human. However, in this specification, as an aid in facilitating the explanation, the color difference signals are employed in lieu of the chromaticity signals I and Q. In such cases, the explanation of signal transform is merely omitted one time, and no problem occurs with the explanation of how the endoscope system operates.

The color image signals (i.e., the luminance signal Y1 and the color difference signals R1−Y1 and B1−Y1), which are made up of color image signal components corresponding to respective pixels and have been obtained from the signal processing circuit 141, are digitized by the analog-to-digital converting circuit 142. The thus obtained color image signals are stored in the ordinary image memory 143. The color image signals are then fed from the ordinary image memory 143 into the superimposer 151. In the superimposer 151, the color image signals are superimposed upon the pseudo color image signals, which are formed in the manner described later. From the superimposer 151, color image signals (i.e., a luminance signal Y and color difference signals R−Y and B−Y) are obtained. The color image signals having been obtained from the superimposer 151 are fed into the RGB decoder 152 and the monitor 170. How the RGB decoder 152 and the monitor 170 operate will be described later.

How the endoscope system, in which the first embodiment of the apparatus for displaying a fluorescence image in accordance with the present invention is employed, operates when a fluorescence image is to be displayed will be described hereinbelow.

When a fluorescence image is to be displayed, the electric power source 115 for the GaN type of semiconductor laser 114 is driven in accordance with a control signal fed from the controller 160, and the excitation light L3 having a wavelength of 410 nm is produced by the GaN type of semiconductor laser 114. The excitation light L3 passes through a lens 116 and impinges upon the excitation light guide 101b. The excitation light L3 is guided through the excitation light guide 101b to the leading end of the endoscope 100, passes through the illuminating lens 104, and is irradiated to the measuring site 10.

When the measuring site 10 is exposed to the excitation light L3, the fluorescence L4 is produced from the measuring site 10. The fluorescence L4 is converged by the converging lens 106 and impinges upon the leading end of the image fiber 103. The fluorescence L4 then passes through the image fiber 103 and impinges upon the excitation light cut-off filter 121 of the fluorescence imaging unit 120.

Thereafter, the fluorescence L4 is converged by a lens 122 and passes through the mosaic filter 123, which is combined with the CCD image sensor 125. In this manner, an image of the fluorescence L4 is formed on the CCD image sensor 125.

In the signal processing circuit 131, the pseudo color image signals are formed in the manner described below from the image signal values, which have been obtained from the CCD image sensor 125. Specifically, color difference matrix operations according to the NTSC method are performed by utilizing light intensity B2 of fluorescence components, which have wavelengths falling within the blue wavelength region and have passed through the optical filters 124a, 124a, . . . , and light intensity W of fluorescence components, which have wavelengths falling within the entire measurement wavelength region and have passed through the blank areas 124b, 124b, . . . In this manner, a pseudo luminance signal Y2 and pseudo color difference signals R2−Y2 and B2−Y2, which act as the pseudo color image signals, are calculated with matrix operations represented by Formula (2) shown below by utilizing the image signal values corresponding to pixels adjacent to each pixel.

$$\begin{bmatrix} Y2 \\ R2 - Y2 \\ B2 - Y2 \end{bmatrix} = \begin{bmatrix} 0.3 & 0.59 & 0.11 \\ 0.7 & -0.59 & -0.11 \\ -0.3 & -0.59 & 0.89 \end{bmatrix} \begin{bmatrix} W \\ B2 \\ B2 \end{bmatrix} \quad (2)$$

Therefore, the pseudo luminance signal Y2 and the pseudo color difference signals R2−Y2 and B2−Y2 are calculated with the formulas shown below.

Y2=0.3W+0.7B2

R2−Y2=0.7W−0.7B2

B2−Y2=−0.3W+0.3B2

The pseudo color image signals (i.e., the pseudo luminance signal Y2 and the pseudo color difference signals R2−Y2 and B2−Y2), which are made up of pseudo color image signal components corresponding to respective pixels and have been obtained from the signal processing circuit 131, are digitized by the analog-to-digital converting circuit 132. The thus obtained pseudo color image signals are stored in the fluorescence image memory 133. The pseudo color image signals are then fed from the fluorescence image memory 133 into the superimposer 151. In the superimposer 151, the pseudo color image signals are superimposed upon the color image signals, which represent the ordinary image and have been received from the ordinary image memory 143. From the superimposer 151, the color image signals (i.e., the luminance signal Y and the color difference signals R−Y and B−Y) are obtained. The color image signals having been obtained from the superimposer 151 are fed into the RGB decoder 152 and the monitor 170.

In the RGB decoder 152, the color signals R, G, and B representing the ordinary image and the color signals R, G, and B representing the fluorescence image are inversely transformed from the received color image signals (i.e., the luminance signal Y and the color difference signals R−Y and B−Y). The inverse transform is performed with the formulas shown below.

Color difference signal G−Y

=0.51·(color difference signal R−Y)

+0.19·(color difference signal B−Y)

Color signal R

=(color difference signal R−Y)+(luminance signal Y)

Color signal B

=(color difference signal B−Y)+(luminance signal Y)

Color signal G

=(color difference signal G−Y)+(luminance signal Y)

With the formulas shown above, the light intensity W of the entire measurement wavelength region is transformed into the color signal R, and the light intensity B2 of the blue wavelength region is transformed into the color signal B and the color signal G. The color signals R, G, and B are fed into a device (not shown) capable of directly receiving the color signals, such as a printer or an image processing unit.

Also, the monitor 170 is provided with the functions for transforming the color image signals into the color signals and displays an ordinary image 30 and a fluorescence image 31. With the monitor 170, the light intensity W of the entire measurement wavelength region is transformed into the color signal R and is displayed as a red color. The light intensity B2 of the blue wavelength region is transformed into the color signal B and the color signal G and is displayed as a blue color and a green color.

As illustrated in FIG. 3, in the cases of the fluorescence produced from the normal tissues, the light intensity of the blue wavelength region is high. Therefore, in the fluorescence image 31, the ratio of the light intensity B2 of the blue wavelength region to the light intensity W of the entire measurement wavelength region is equal to approximately 1:1.5, and the color signal ratio B:G:R becomes equal to 1:1:1.5. As a result, the display color of the fluorescence image 31 of the fluorescence produced from the normal tissues is pink close to white. In the cases of the fluorescence produced from the diseased tissues, the light intensity of the blue wavelength region is not much high. Therefore, in the fluorescence image 31, the ratio of the light intensity B2 of the blue wavelength region to the light intensity W of the entire measurement wavelength region is equal to approximately 1:2, and the color signal ratio B:G:R becomes equal to 1:1:2. As a result, the display color of the fluorescence image 31 of the fluorescence produced from the diseased tissues is pink close to red. Accordingly, the person who sees the displayed image is capable of presuming the tissue condition at the measuring site 10 in accordance with the display color of the fluorescence image 31.

Figure 5:
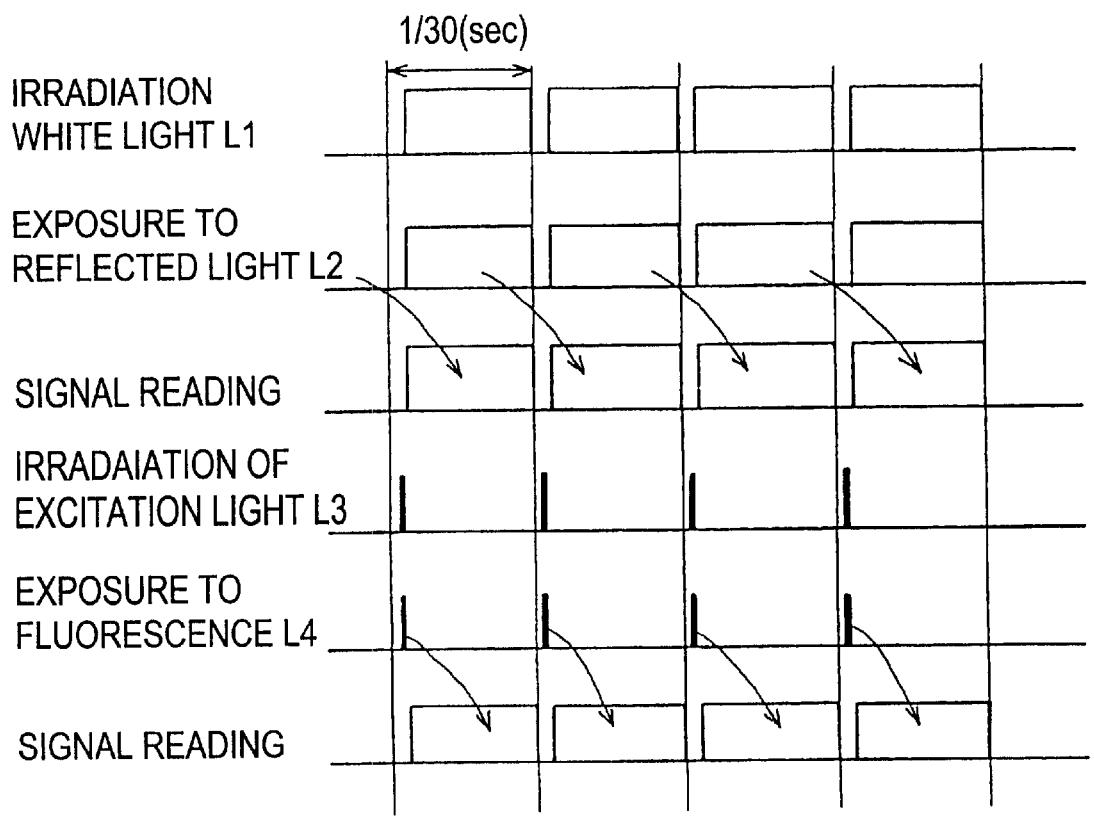
FIG. 5 is a timing chart employed in the endoscope system, in which the first embodiment of the apparatus for displaying a fluorescence image in accordance with the present invention is employed.

The series of operations described above are controlled by the controller 160 and are performed in accordance with a timing chart illustrated in FIG. 5. As illustrated in FIG. 5, the irradiation of the white light L1 and the exposure of the CCD image sensor 108 to the reflected light L2 are performed synchronously every ⅟30 second, and signal reading from the CCD image sensor 108 is then performed. The irradiation of the excitation light L3 and the exposure of the CCD image sensor 125 to the fluorescence L4 are performed during a period corresponding to a vertical blanking period in a television system, and signal reading from the CCD image sensor 125 is then performed. Therefore, the acquisition of the ordinary image is not obstructed by the acquisition of the fluorescence image. Also, since each of the ordinary image and the fluorescence image is acquired every ⅟30 second, the ordinary image 30 and the fluorescence image 31 are displayed on the monitor 170 as dynamic images, which are updated every ⅟30 second.

As described above, with the endoscope system, in which the first embodiment of the apparatus for displaying fluorescence information in accordance with the present invention is employed, the light intensity W of the entire measurement wavelength region and the light intensity B2 of the blue wavelength region, which is a comparatively short wavelength region, are detected from the fluorescence L4, which is produced from the measuring site 10 when the measuring site 10 is exposed to the excitation light L3. Also, the display color in accordance with the ratio between the light intensity W of the entire measurement wavelength region and the light intensity B2 of the comparatively short wavelength region is displayed by the utilization of the additive color mixture process. In this manner, the light intensity of the entire measurement wavelength region is capable of being utilized. Therefore, the efficiency, with which the fluorescence L4 is utilized, is capable of being kept higher than with conventional techniques, and the signal-to-noise ratio of the displayed fluorescence image is capable of being enhanced.

Also, the entire measurement wavelength region described above is the entire visible wavelength region excluding the wavelength region of the excitation light L3 in the vicinity of 410 nm. Therefore, the detection of the light intensity is not obstructed by the excitation light L3, and the fluorescence having been produced from the measuring site 10 is capable of being utilized efficiently.

Figure 6:
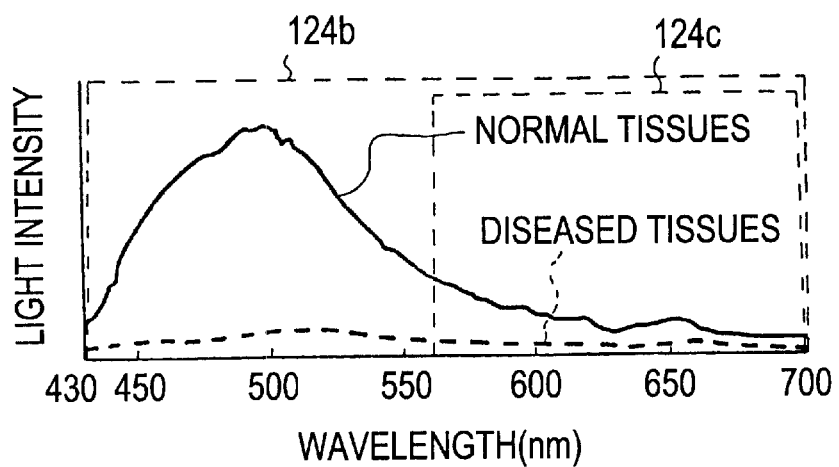
FIG. 6 is a graph showing transmission wavelength regions of optical filters constituting a different example of a mosaic filter for a fluorescence image employed in the endoscope system, in which the first embodiment of the apparatus for displaying a fluorescence image in accordance with the present invention is employed.

Further, in the first embodiment, the mosaic filter 123 is constituted of the optical filters 124*a*, 124*a*, . . . , which are the band-pass filters for transmitting only light having wavelengths falling within the comparatively short wavelength region of 430 nm to 530 nm, and the blank areas 124*b*, 124*b*, for transmitting light having wavelengths falling within the entire measurement wavelength region. Alternatively, as illustrated in FIG. 6, the mosaic filter 123 may be replaced by a mosaic filter constituted of optical filters 124*c*, 124*c*, . . . , which transmit only light having wavelengths falling within a comparatively long wavelength region of 560 nm to 700 nm, and the blank areas 124*b*, 124*b*, . . . In such cases, the light intensity of the entire measurement wavelength region and the light intensity of the comparatively long wavelength region may be detected, and the display color in accordance with the ratio between the two light intensities may be displayed by the utilization of the additive color mixture process. In this manner, the same effects as those described above are capable of being obtained.

Figure 7:
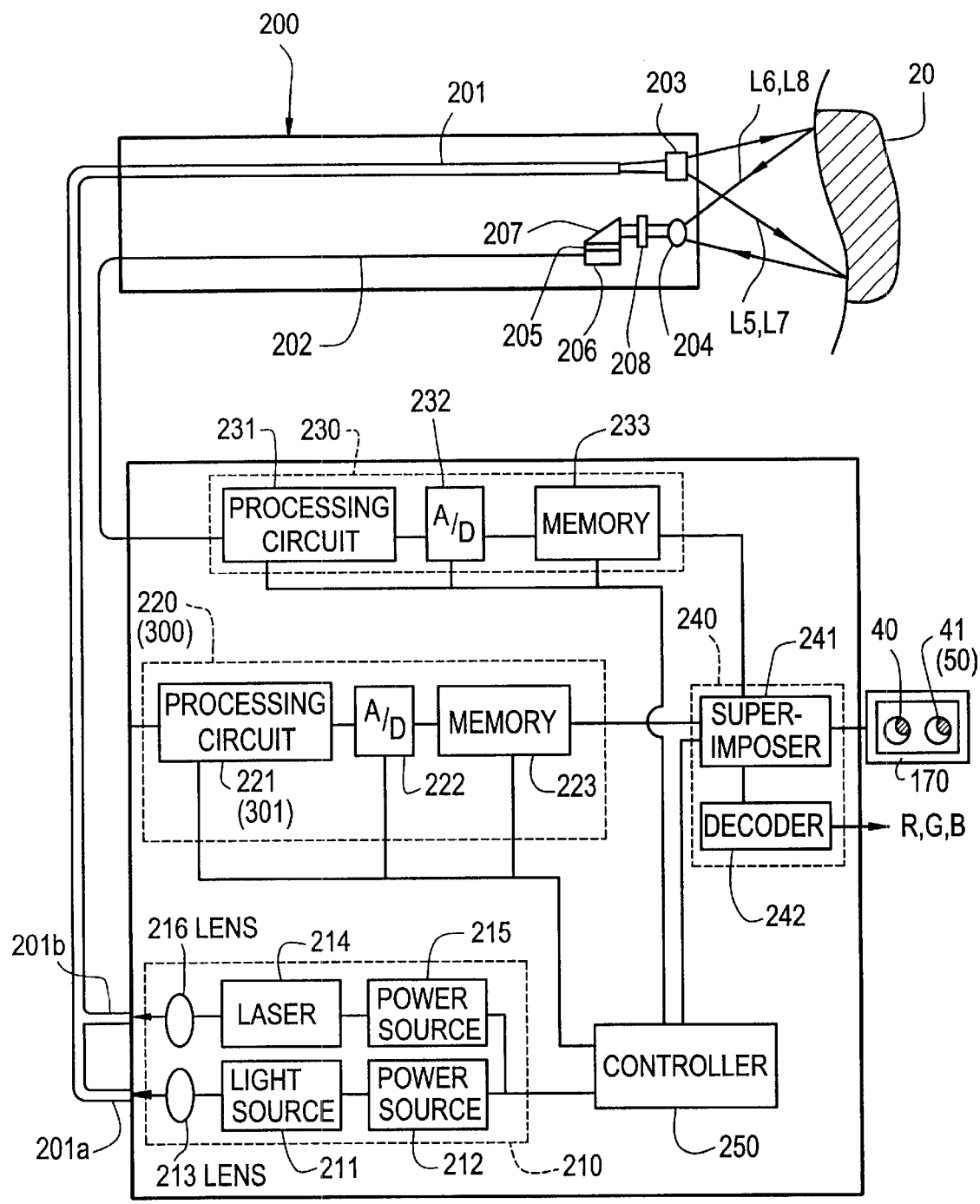
FIG. 7 is a schematic view showing an endoscope system, in which a second embodiment of the apparatus for displaying a fluorescence image in accordance with the present invention is employed.
Figure 8:
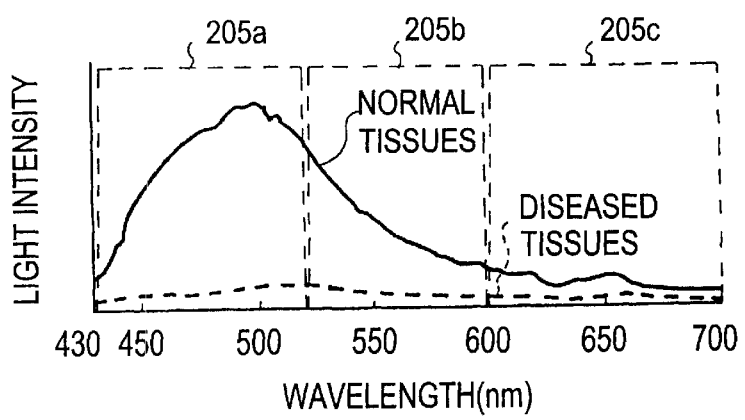
FIG. 8 is a graph showing transmission wavelength regions of optical filters constituting a mosaic filter for a fluorescence image employed in the endoscope system, in which the second embodiment of the apparatus for displaying a fluorescence image in accordance with the present invention is employed.
Figure 9:
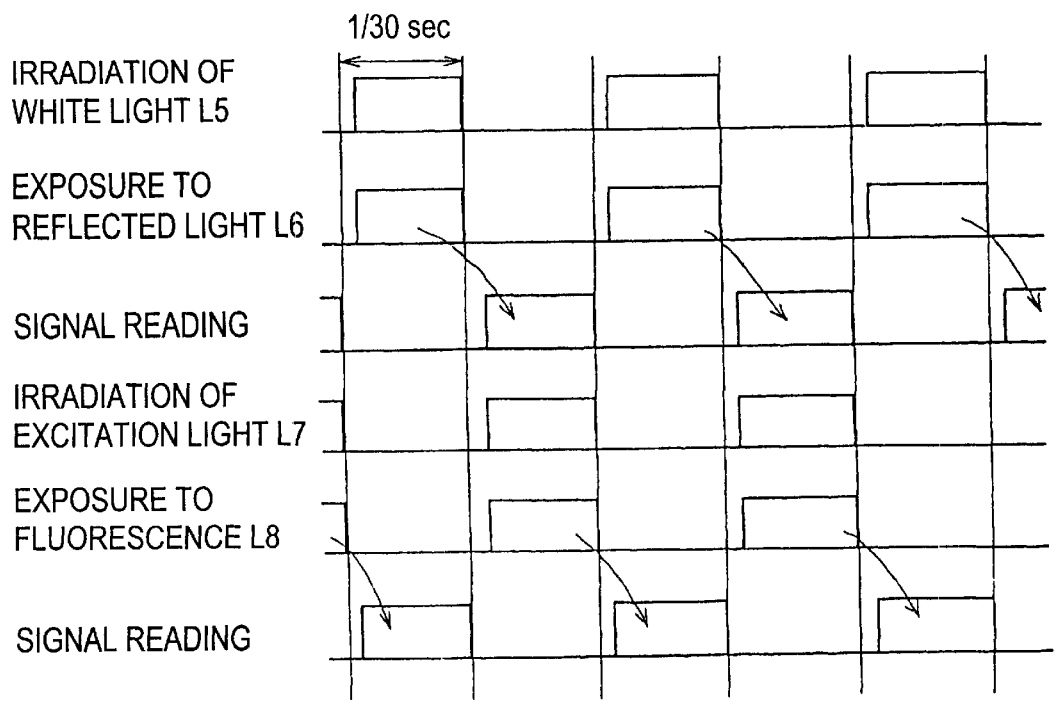
FIG. 9 is a timing chart employed in the endoscope system, in which the second embodiment of the apparatus for displaying a fluorescence image in accordance with the present invention is employed.
Figure 10:
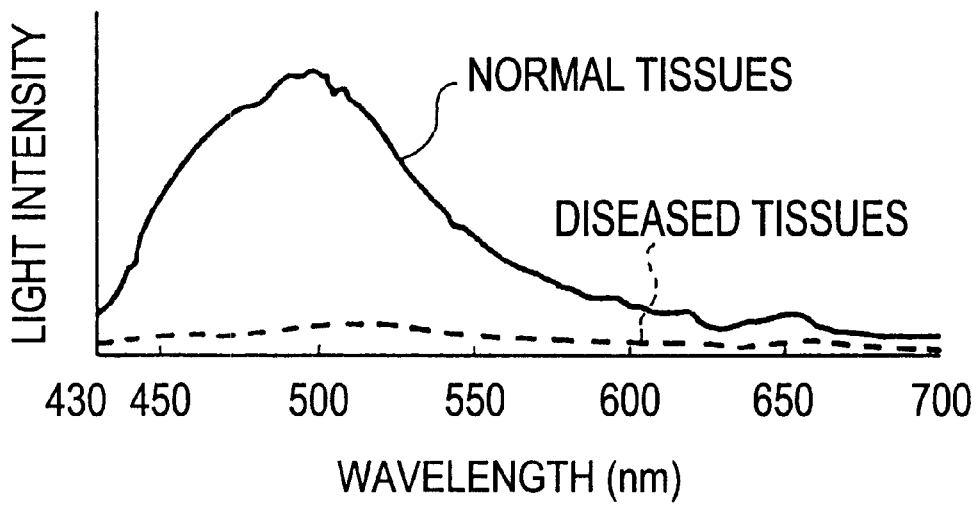
FIG. 10 is a graph showing spectral intensity distributions of fluorescence produced from normal tissues and fluorescence produced from diseased tissues.
Figure 11:
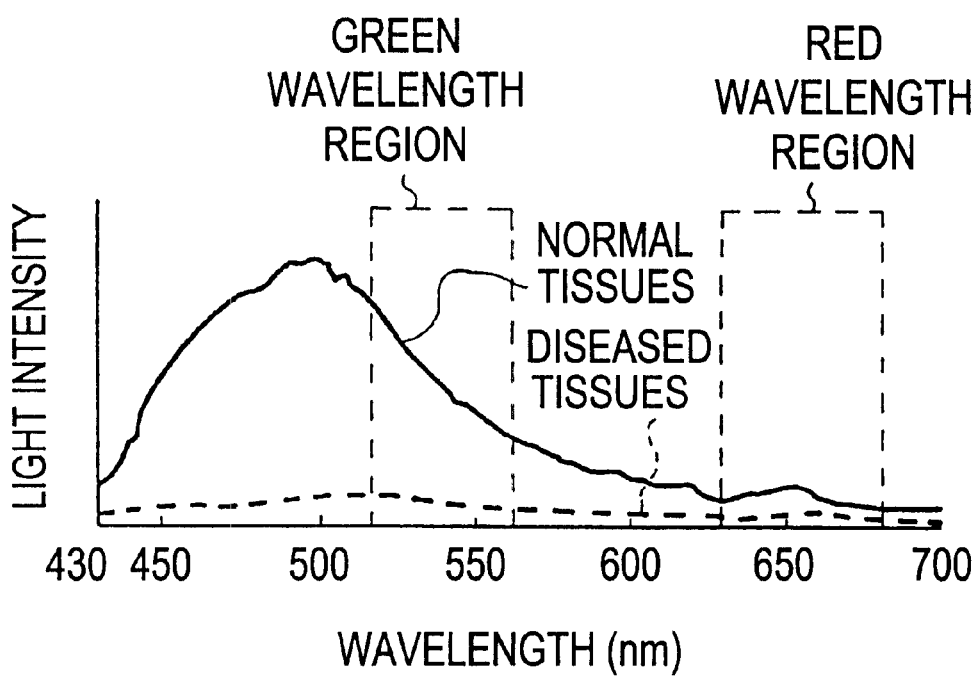
FIG. 11 is a graph showing wavelength regions employed in a conventional apparatus for displaying a fluorescence image.
Figure 12:
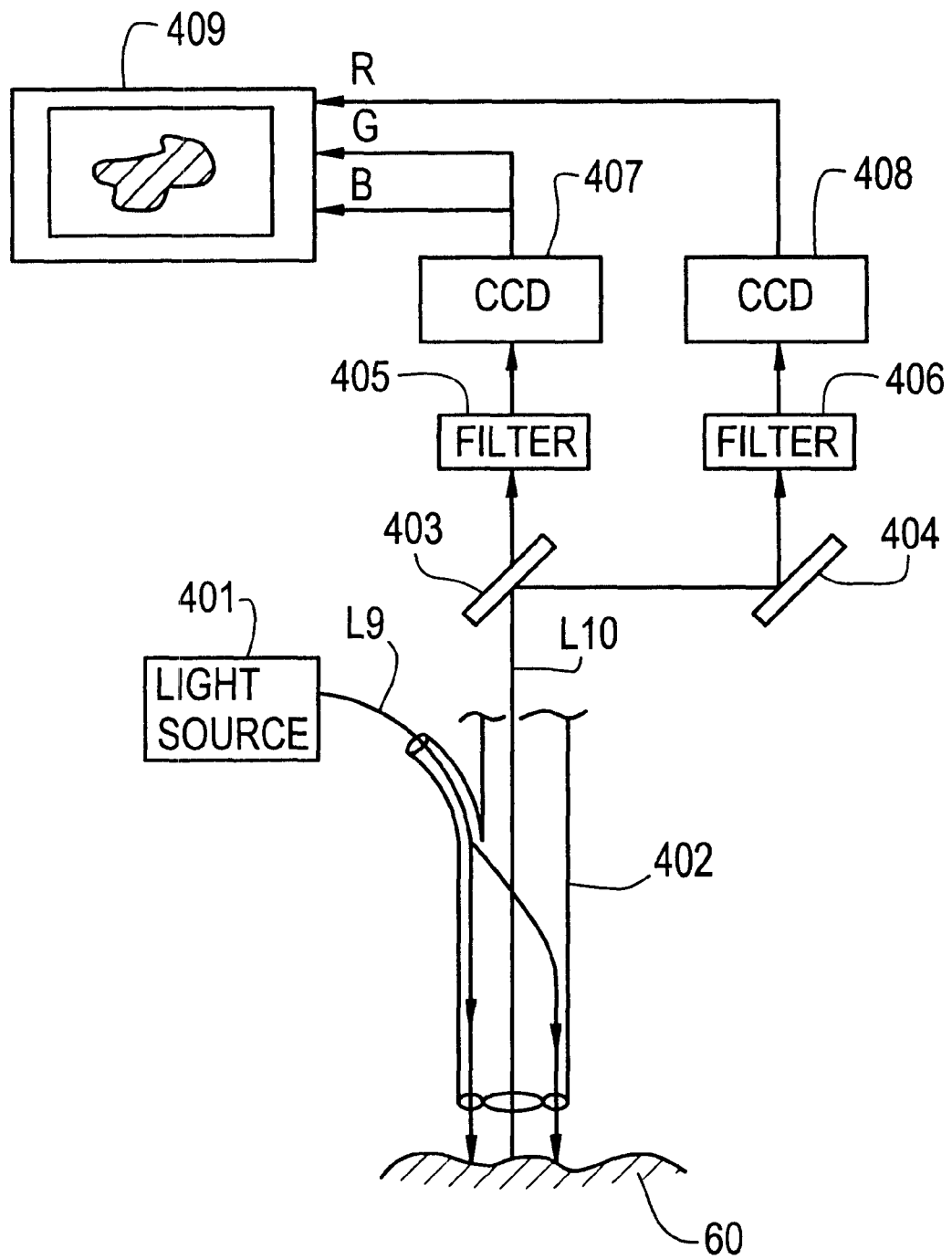
FIG. 12 is a schematic view showing a conventional apparatus for displaying a fluorescence image.

An endoscope system, in which a second embodiment of the apparatus for displaying a fluorescence image in accordance with the present invention is employed, will be described hereinbelow with reference to FIG. 7 to FIG. 9. FIG. 7 is a schematic view showing the endoscope system, in which the second embodiment of the apparatus for displaying a fluorescence image in accordance with the present invention is employed. In the endoscope system, in which the second embodiment of the apparatus for displaying a fluorescence image in accordance with the present invention is employed, excitation light is irradiated to a measuring site in a living body. Fluorescence produced from the measuring site is received by a CCD image sensor, which is located at a leading end of an endoscope and is utilized also for detecting an ordinary image. In this manner, a detected fluorescence image is displayed on the monitor.

The endoscope system, in which the second embodiment of the apparatus for displaying fluorescence information in accordance with the present invention is employed, comprises an endoscope 200 to be inserted into a region of a patient, which region is considered as being a diseased part, and an illuminating unit 210 provided with light sources for producing white light, which is used when an ordinary image is to be displayed, and the excitation light, which is used when fluorescence information is to be displayed. The endoscope system also comprises a fluorescence image processing unit 220 for performing image processing for displaying a fluorescence image as a pseudo color image, and an ordinary image processing unit 230 for performing image processing for displaying an ordinary image as a color image. The endoscope system further comprises a display image processing unit 240 for superimposing the ordinary image and the fluorescence image one upon the other. The endoscope system still further comprises a controller 250, which is connected to the respective units and controls operation timings. The endoscope system also comprises the monitor 170 for displaying the display images, which have been obtained from the processing performed by the display image processing unit 240.

A light guide 201 and a CCD cable 202 extend in the endoscope 200 up to a leading end of the endoscope 200. An illuminating lens 203 is located at a leading end of the light guide 201, i.e. at the leading end of the endoscope 200. An objective lens 204 is located at a leading end of the CCD cable 202, i.e. at the leading end of the endoscope 200. A CCD image sensor 206, which is constituted of a cooled, back exposure type of CCD image sensor, is connected to the leading end of the CCD cable 202. A mosaic filter 205, which comprises three primary color optical filters arrayed in a mosaic form, is combined with the CCD image sensor 206. Also, a prism 207 is mounted on the CCD image sensor 206. An excitation light cut-off filter 208 for filtering out light, which has wavelengths falling within a wavelength region of at most 430 nm in the vicinity of the wavelength of the excitation light, from the fluorescence is located between the prism 207 and the objective lens 204.

The mosaic filter 205 comprises optical filters 205*a*, 205*a*, . . . optical filters 205*b*, 205*b*, . . . , and optical filters 205*c*, 205*c*, . . . , which are arrayed alternately in the same manner as that in the mosaic filter 107 illustrated in FIG. 2. The optical filters 205*a*, 205*a*, . . . are band pass filters for transmitting only light having wavelengths falling within the range of 430 nm to 520 nm. The optical filters 205b, 205b, . . . are band pass filters for transmitting only light having wavelengths falling within the range of 520 nm to 600 nm. The optical filters 205c,, 205c, . . . are band pass filters for transmitting only light having wavelengths falling within the range of 600 nm to 700 nm. The transmission wavelength regions of the optical filters 205a, 205a, . . . , the optical filters 205b, 205b, . . . , and the optical filters 205c, 205c, . . . are illustrated in FIG. 8.

The light guide 201 comprises a white light guide 201a, which is constituted of a compound glass fiber, and an excitation light guide 201b, which is constituted of a quartz glass fiber. The white light guide 201a and the excitation light guide 201b are bundled together in a cable-like form to constitute the light guide 201. The white light guide 201a and the excitation light guide 201b are connected to the illuminating unit 210. A tail end of the CCD cable 202 is connected to the fluorescence image processing unit 220 and the ordinary image processing unit 230.

The illuminating unit 210 comprises a white light source 211 for producing white light L5, which is used when an ordinary image is to be displayed, and an electric power source 212, which is electrically connected to the white light source 211. The illuminating unit 210 also comprises a GaN type of semiconductor laser 214 for producing excitation light L7, which is used when a fluorescence image is to be displayed, and an electric power source 215, which is electrically connected to the GaN type of semiconductor laser 214.

The fluorescence image processing unit 220 comprises a signal processing circuit 221 for forming pseudo color image signals from fluorescence image signal values, which have been obtained from the CCD image sensor 206. The fluorescence image processing unit 220 also comprises an analog-to-digital converting circuit 222 for digitizing the pseudo color image signals, which have been obtained from the signal processing circuit 221. The fluorescence image processing unit 220 further comprises a fluorescence image memory 223 for storing the digital pseudo color image signals, which have been obtained from the analog-to-digital converting circuit 222.

The ordinary image processing unit 230 comprises a signal processing circuit 231 for forming color image signals from ordinary image signal values, which have been obtained from the CCD image sensor 206. The ordinary image processing unit 230 also comprises an analog-to-digital converting circuit 232 for digitizing the color image signals, which have been obtained from the signal processing circuit 231. The ordinary image processing unit 230 further comprises an ordinary image memory 233 for storing the digital color image signals, which have been obtained from the analog-to-digital converting circuit 232.

The display image processing unit 240 comprises a superimposer 241 for superimposing the pseudo color image signals, which have been received from the fluorescence image memory 223, and the color image signals, which have been received from the ordinary image memory 233, one upon the other. The display image processing unit 240 also comprises an RGB decoder 242 for transforming the superimposed image signals into color signals.

How the endoscope system, in which the second embodiment of the apparatus for displaying a fluorescence image in accordance with the present invention is employed, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 250, and the white light L5 is produced by the white light source 211. The white light L5 passes through a lens 213 and impinges upon the white light guide 201a. The white light L5 is guided through the white light guide 201a to the leading end of the endoscope 200, passes through the illuminating lens 203, and is irradiated to a measuring site 20. The white light L5 is reflected as reflected light L6 from the measuring site 20. The reflected light L6 is converged by the objective lens 204, passes through the excitation light cut-off filter 208, and is then reflected by the prism 207. The reflected light L6 then passes through the mosaic filter 205, and an image of the reflected light L6 is formed on the CCD image sensor 206.

In the signal processing circuit 231, the color image signals are formed from the image signal values, which have been obtained from the CCD image sensor 206, in the same manner as that in the signal processing circuit 141 shown in FIG. 1. Specifically, the color difference matrix operations according to the NTSC method are performed by utilizing light intensity B3 of light components, which have wavelengths falling within the blue wavelength region and have passed through the optical filters 205a, 205a, . . . , light intensity G3 of light components, which have wavelengths falling within the green wavelength region and have passed through the optical filters 205b, 205b, . . . , and light intensity R3 of light components, which have wavelengths falling within the red wavelength region and have passed through the optical filters 205c, 205c, . . . In this manner, a luminance signal Y3 and color difference signals R3−Y3 and B3−Y3, which act as the color image signals, are calculated.

The color image signals (i.e., the luminance signal Y3 and the color difference signals R3−Y3 and B3−Y3), which are made up of color image signal components corresponding to respective pixels and have been obtained from the signal processing circuit 231, are digitized by the analog-to-digital converting circuit 232. The thus obtained color image signals are stored in the ordinary image memory 233. The color image signals are then fed from the ordinary image memory 233 into the superimposer 241. In the superimposer 241, the color image signals are superimposed upon the pseudo color image signals, which represent the fluorescence image and are formed in the manner described later. The color image signals having been obtained from the superimposer 241 are fed into the RGB decoder 242 and the monitor 170. How the RGB decoder 242 and the monitor 170 operate will be described later.

How the endoscope system, in which the second embodiment of the apparatus for displaying a fluorescence image in accordance with the present invention is employed, operates when a fluorescence image is to be displayed will be described hereinbelow.

When a fluorescence image is to be displayed, the electric power source 215 for the GaN type of semiconductor laser 214 is driven in accordance with a control signal fed from the controller 250, and the excitation light L7 having a wavelength of 410 nm is produced by the GaN type of semiconductor laser 214. The excitation light L7 passes through a lens 216 and impinges upon the excitation light guide 201b. The excitation light L7 is guided through the excitation light guide 201b to the leading end of the endoscope 200, passes through the illuminating lens 203, and is irradiated to the measuring site 20.

When the measuring site 20 is exposed to the excitation light L7, fluorescence L8 is produced from the measuring site 20. The fluorescence L8 is converged by the converging lens 204, passes through the excitation light cut-off filter

208, and is then reflected by the prism 207. The fluorescence L8 then passes through the mosaic filter 205, and an image of the fluorescence L8 is formed on the CCD image sensor 206.

The timings, with which the imaging of the ordinary image with irradiation of the white light L5 and the imaging of the fluorescence image with irradiation of the excitation light L7 are performed, are controlled by the controller 250. The imaging operations are performed in accordance with a timing chart illustrated in FIG. 9. As illustrated in FIG. 9, the operation for irradiating the white light L5 and exposing the CCD image sensor 206 to the ordinary image and the operation for irradiating the excitation light L7 and exposing the CCD image sensor 206 to the fluorescence image are performed alternately every 1/30 second. The image signal representing the ordinary image is fed into the signal processing circuit 231, and the image signal representing the fluorescence image is fed into the signal processing circuit 221. Therefore, each of the ordinary image and the fluorescence image is acquired every 1/15 second, and an ordinary image 40 and a fluorescence image 41 are displayed on the monitor 170 as dynamic images, which are updated every 1/15 second.

In the signal processing circuit 221, the pseudo color image signals are formed from the image signal values, which have been obtained from the CCD image sensor 206. Specifically, a pseudo luminance signal Y4 and pseudo color difference signals R4−Y4 and B4−Y4, which act as the pseudo color image signals, are calculated with operations described below by utilizing light intensity B4 of fluorescence components, which have wavelengths falling within the blue wavelength region and have passed through the optical filters 205a, 205a, . . . , light intensity G4 of fluorescence components, which have wavelengths falling within the green wavelength region and have passed through the optical filters 205b, 205b, . . . , and light intensity R4 of fluorescence components, which have wavelengths falling within the red wavelength region and have passed through the optical filters 205c, 205c, . . .

Firstly, light intensity W', which corresponds to the light intensity of fluorescence components, which have wavelengths falling within the entire measurement wavelength region, is calculated with the formula shown below.

$$W'=B4+G4+R4$$

Thereafter, the pseudo luminance signal Y4 and the pseudo color difference signals R4−Y4 and B4−Y4 are calculated with matrix operations represented by Formula (3) shown below by utilizing the image signal values corresponding to pixels adjacent to each pixel.

$$\begin{bmatrix} Y4 \\ R4-Y4 \\ B4-Y4 \end{bmatrix} = \begin{bmatrix} 0.3 & 0.59 & 0.11 \\ 0.7 & -0.59 & -0.11 \\ -0.3 & -0.59 & 0.89 \end{bmatrix} \begin{bmatrix} W' \\ B4 \\ B4 \end{bmatrix} \quad (3)$$

Therefore, the pseudo luminance signal Y4 and the pseudo color difference signals R4−Y4 and B4−Y4 are calculated with the formulas shown below.

$$Y4=0.3W'+0.7B4$$

$$R4-Y4=0.7W'-0.70B4$$

$$B4-Y4=-0.3W'+0.3B4$$

The pseudo color image signals (i.e., the pseudo luminance signal Y4 and the pseudo color difference signals R4−Y4 and B4−Y4), which are made up of pseudo color image signal components corresponding to respective pixels and have been obtained from the signal processing circuit 221, are digitized by the analog-to-digital converting circuit 222. The thus obtained pseudo color image signals are stored in the fluorescence image memory 223. The pseudo color image signals are then fed from the fluorescence image memory 223 into the superimposer 241. In the superimposer 241, the pseudo color image signals are superimposed upon the color image signals (i.e., the luminance signal Y3 and the color difference signals R3−Y3 and B3−Y3), which represent the ordinary image and have been received from the ordinary image memory 233. The color image signals having been obtained from the superimposer 241 are fed into the RGB decoder 242 and the monitor 170.

In the RGB decoder 242, in the same manner as that in the RGB decoder 152 shown in FIG. 1, the color image signals are decoded into the color signals R, G, and B. The thus obtained color signals R, G, and B are fed into a device (not shown) capable of directly receiving the color signals, such as a printer or an image processing unit.

The monitor 170 decodes the color image signals into the color signals R, G, and B and displays the ordinary image 40 and the fluorescence image 41.

In the fluorescence image 41, the light intensity W' (=B4+G4+R4) is displayed as the color signal R. Also, the light intensity B4 of the blue wavelength region is displayed as the color signal B and the color signal G.

Each of the ordinary image and the fluorescence image is acquired every 1/15 second. Therefore, the ordinary image 40 and the fluorescence image 41 are displayed on the monitor 170 as dynamic images, which are updated every 1/15 second.

Accordingly, the display color of the fluorescence image 31 of the fluorescence produced from the normal tissues is pink close to white. Also, the display color of the fluorescence image 31 of the fluorescence produced from the diseased tissues is pink close to red. In this manner, the same effects as those with the first embodiment shown in FIG. 1 are capable of being obtained.

Also, with the second embodiment, the CCD image sensor for detecting the fluorescence image is utilized also as the CCD image sensor for detecting the ordinary image. Therefore, the production cost of the apparatus for displaying a fluorescence image is capable of being kept low.

An endoscope system, in which a third embodiment of the apparatus for displaying a fluorescence image in accordance with the present invention is employed, will be described hereinbelow with reference to FIG. 7. The third embodiment is basically identical with the second embodiment of FIG. 7, except for the elements numbered with the reference numerals indicated in parentheses.

In the third embodiment of the apparatus for displaying a fluorescence image in accordance with the present invention, a fluorescence image is displayed with a display color in accordance with the ratio among the light intensity of a wavelength region of 430 nm to 520 nm, the light intensity of a wavelength region of 520 nm to 600 nm, and the light intensity of a wavelength region of 600 nm to 700 nm. The display color is displayed by utilizing the additive color mixture process.

A fluorescence image processing unit 300 comprises a signal processing circuit 301 for forming color image signals from the fluorescence image signal values, which have been obtained from the CCD image sensor 206. The fluorescence image processing unit 300 also comprises the analog-to-digital converting circuit 222 for digitizing the color image signals, which have been obtained from the signal processing circuit 301. The fluorescence image processing unit 300 further comprises the fluorescence image memory 223 for storing the digital color image signals, which have been obtained from the analog-to-digital converting circuit 222.

When a fluorescence image is to be displayed, in the signal processing circuit 301, the color image signals are formed from the image signal values, which have been obtained from the CCD image sensor 206. Specifically, a luminance signal Y5 and color difference signals R5–Y5 and B5–Y5, which act as the color image signals, are calculated with matrix operations by utilizing the light intensity B4 of fluorescence components, which have wavelengths falling within the blue wavelength region and have passed through the optical filters 205a, 205a, . . . , light intensity G4 of fluorescence components, which have wavelengths falling within the green wavelength region and have passed through the optical filters 205b, 205b, . . . , and light intensity R4 of fluorescence components, which have wavelengths falling within the red wavelength region and have passed through the optical filters 205c, 205c, . . . The matrix operations are performed with Formula (4) shown below.

$$\begin{bmatrix} Y5 \\ R5 - Y5 \\ B5 - Y5 \end{bmatrix} = \begin{bmatrix} 0.3 & 0.59 & 0.11 \\ 0.7 & -0.59 & -0.11 \\ -0.3 & -0.59 & 0.89 \end{bmatrix} \begin{bmatrix} R4 \\ G4 \\ B4 \end{bmatrix} \quad (4)$$

Therefore, the luminance signal Y5 and the color difference signals R5–Y5 and B5–Y5 are calculated with the formulas shown below.

Y5=0.30R4+0.59G4+0.11B4

R5–Y5=0.70R4–0.59G4–0.11B4

B5–Y5=–0.30R4–0.59G4+0.89B4

The color image signals (i.e., the luminance signal Y5 and the color difference signals R5–Y5 and B5–Y5), which are made up of color image signal components corresponding to respective pixels and have been obtained from the signal processing circuit 301, are digitized by the analog-to-digital converting circuit 222. The thus obtained color image signals are stored in the fluorescence image memory 223. The color image signals are then fed from the fluorescence image memory 223 into the superimposer 241. In the superimposer 241, the color image signals are superimposed upon the color image signals (i.e., the luminance signal Y3 and the color difference signals R3–Y3 and B3–Y3), which represent the ordinary image and have been received from the ordinary image memory 233. The color image signals having been obtained from the superimposer 241 are fed into the RGB decoder 242 and the monitor 170. The color image signals are utilized for displaying the ordinary image 40 and a fluorescence image 50 on the monitor 170.

In the fluorescence image 50, as in the ordinary image 40, the light intensity B4 of the wavelength region of 430 nm to 520 nm is displayed as the color signal B. The light intensity G4 of the wavelength region of 520 nm to 600 nm is displayed as the color signal G. Also, the light intensity R4 of the wavelength region of 600 nm to 700 nm is displayed as the color signal R.

Accordingly, the display color of the fluorescence image 50 of the fluorescence produced from the normal tissues is cyan. Also, the display color of the fluorescence image 50 of the fluorescence produced from the diseased tissues is a color close to white. In this manner, the same effects as those with the second embodiment shown in FIG. 7 are capable of being obtained. Also, a fine difference in light intensity between the wavelength regions of the fluorescence having been produced from the measuring site is capable of being displayed as a difference in tint of the display color.

In each of the embodiments described above, the coefficients in the matrix operations for transforming each of the light intensities into the color signals are capable of being set at various appropriate values. The tint corresponding to each of the light intensities is capable of being selected arbitrarily by appropriately setting the coefficients in the matrix operations. For example, the coefficients in the matrix operations may be set such that the display color for the fluorescence having been produced from the normal tissues may be white. In such cases, the person who sees the displayed fluorescence image is capable of recognizing with an enhanced reliability as to whether the fluorescence, which has been produced from the measuring site, is the fluorescence produced from the normal tissues or the fluorescence produced from the diseased tissues.

In addition, all of the contents of Japanese Patent Application No. 11(1999)-342932 are incorporated into this specification by reference.

What is claimed is:

1. An apparatus for displaying a fluorescence image, comprising:

i) excitation light irradiating means for irradiating excitation light to a region of interest in a living body, the excitation light causing the region of interest to produce intrinsic fluorescence, and ii) image displaying means for acquiring image information in accordance with the intrinsic fluorescence, which is produced from the region of interest when the region of interest is exposed to the excitation light, and displaying the acquired image information, wherein the image displaying means comprises:

a) first light intensity detecting means for an entire measurement wavelength region, the first light intensity detecting means detecting a first light intensity of intrinsic fluorescence components of the intrinsic fluorescence, wherein the intrinsic fluorescence components have wavelengths falling within the entire measurement wavelength region, b) second light intensity detecting means for a partial measurement wavelength region, the second light intensity detecting means detecting a second light intensity of intrinsic fluorescence components of the intrinsic fluorescence, wherein the intrinsic fluorescence components have wavelengths falling within either one of a comparatively short wavelength region and a comparatively long wavelength region, and c) display means for displaying a plurality of display colors in accordance with a ratio between the first light intensity detected by the first light intensity detecting means for the entire measurement wavelength region, and the second light intensity detected by the second light intensity detecting means for the partial measurement wavelength region, the display colors being displayed by the utilization of an additive color mixture process, wherein the first light intensity detected by the first light intensity detecting means for the entire measurement wavelength region is displayed as one of the display colors, and the second light intensity detected by the second light intensity detecting means for the partial measurement wavelength region is displayed as the other display colors.

2. An apparatus as defined in claim 1, wherein the first light intensity is a light intensity of intrinsic fluorescence components of the intrinsic fluorescence, and the intrinsic fluorescence components have wavelengths falling within an entire visible wavelength region excluding the vicinity of the wavelength region of the excitation light.

3. An apparatus for displaying a fluorescence image, comprising:

i) excitation light irradiating means for irradiating excitation light to a region of interest in a living body, the excitation light causing the region of interest to produce intrinsic fluorescence, and ii) image displaying means for acquiring image information in accordance with the intrinsic fluorescence, which is produced from the region of interest when the region of interest is exposed to the excitation light, and displaying the acquired image information, wherein the image displaying means comprises:

a) first light intensity detecting means for a red region, the first light intensity detecting means detecting a first light intensity of intrinsic fluorescence components of the intrinsic fluorescence, wherein the intrinsic fluorescence components have wavelengths falling within the red wavelength region, b) second light intensity detecting means for a green region, the second light intensity detecting means detecting a second light intensity of intrinsic fluorescence components of the intrinsic fluorescence, wherein the intrinsic fluorescence components have wavelengths falling within the green wavelength region, c) third light intensity detecting means for a blue region, the third light intensity detecting means detecting a third light intensity of intrinsic fluorescence components of the intrinsic fluorescence, wherein the intrinsic fluorescence components have wavelengths falling within the blue wavelength region, and d) display means for displaying display colors in accordance with a ratio among the first light intensity detected by the first light intensity detecting means for the red region, the second light intensity detected by the second light intensity detecting means for the green region, and the third light intensity detected by the third light intensity detecting means for the blue region, the display colors being displayed by the utilization of an additive color mixture process, wherein a light intensity corresponding to the intrinsic fluorescence components having wavelengths falling within an entire measurement wavelength region is displayed as one of the display colors, and the third light intensity detected by the third light intensity detecting means for the blue measurement wavelength region is displayed as the other display colors.

4. An apparatus as defined in claim 3, wherein a sum of the first light intensity detected by the first light intensity detecting means for the red region, the second light intensity detected by the light intensity detecting means for the green region, and third the light intensity detected by the third light intensity detecting means for the blue region, is the light intensity of intrinsic fluorescence components of the intrinsic fluorescence, and the intrinsic fluorescence components have wavelengths falling within the entire measurement wavelength region excluding the wavelength region of the excitation light.

5. An apparatus as defined in claim 1, 2, 3, or 4 wherein the display means is provided with a matrix operation circuit and is constituted such that a color corresponding to each of the light intensities is capable of being selected arbitrarily by appropriately setting coefficients of an operation formula in the matrix operation circuit.

* * * * *